United States Patent [19]
Lyle et al.

[11] Patent Number: 5,346,686
[45] Date of Patent: Sep. 13, 1994

[54] LABELLED INTERLEUKIN-8 AND MEDICAL USES THEREOF

[75] Inventors: Leon R. Lyle, Webster Groves, Mo.; Steven L. Kunkel, Ann Arbor, Mich.

[73] Assignees: Mallinckrodt Medical, Inc., St. Louis, Mo.; Curators of the University of Michigan, Ann Arbor, Mich.

[21] Appl. No.: 956,863

[22] Filed: Oct. 5, 1992

[51] Int. Cl.⁵ .............................................. A61K 49/02
[52] U.S. Cl. .................................................. 424/1.41
[58] Field of Search ........................ 424/1.1, 9, 1.41; 530/351

[56] References Cited

U.S. PATENT DOCUMENTS

| | | | |
|---|---|---|---|
| 4,659,839 | 4/1987 | Nicolotti et al. | 548/546 |
| 4,732,974 | 3/1988 | Nicolotti et al. | 530/390 |
| 4,832,940 | 5/1989 | Ege | 424/1.1 |
| 4,837,003 | 6/1989 | Nicolotti | 424/1.1 |
| 4,926,869 | 5/1990 | Rubin et al. | 128/654 |
| 4,965,392 | 10/1990 | Fritzberg et al. | 558/254 |
| 4,986,979 | 1/1991 | Morgan, Jr. et al. | 424/1.1 |
| 5,037,630 | 8/1991 | Fritzberg et al. | 424/1.1 |
| 5,120,525 | 6/1992 | Goldenberg | 424/1.1 |
| 5,225,180 | 6/1993 | Dean et al. | 424/1.1 |

FOREIGN PATENT DOCUMENTS

| | | |
|---|---|---|
| 0284071 | 9/1988 | European Pat. Off. . |
| 9013317 | 11/1990 | PCT Int'l Appl. . |
| 9108231 | 6/1991 | World Int. Prop. O. ... C07K 13/00 |
| 9108483 | 6/1991 | PCT Int'l Appl. . |
| 9101144 | 2/1991 | World Int. Prop. O. ... A61K 43/00 |

OTHER PUBLICATIONS

Besemer et al., "Specific Binding, Internalization, & Degradation of Human Neutrophil Activating Factor by Human Polymorphonuclear Leukocytes," *J. Biol. Chem.* 264(29), Oct. 15, 1989, pp. 17409–17415.

Darbonne et al., "Red Blood Cells Are a Sink for Interleukin 8 . . . ," *J. Clin. Invest.* 88, Oct. 1991, pp. 1362–1369.

Grob et al., "Characterization of a Receptor for Human Monocyte-Derived Neutrophil Chemotactic Factor/Interleukin-8," *J. Biol. Chem.* 265(14) May 15, 1990, pp. 8311–8316.

*Primary Examiner*—Richard D. Lovering
*Assistant Examiner*—Lara E. Chapman
*Attorney, Agent, or Firm*—Rothwell, Figg, Ernst & Kurz

[57] ABSTRACT

A method of imaging a target site in an animal's body in which a labelled CXC chemokine is introduced into the animal's body and allowed to accumulate at a target site which includes Interleukin-8 receptor molecules. The accumulated, labelled CXC chemokine is then detected so as to image the target site of the body.

23 Claims, 8 Drawing Sheets

LABELLED INTERLEUKIN-8 AND MEDICAL USES THEREOF

BACKGROUND OF THE INVENTION

1. Field of the Invention

The present invention relates to the field of labelled peptides, peptides carrying radioactive agents, and medical uses thereof.

2. Description of the Background Art

Labelled peptides and peptides carrying radioactive agents have various therapeutic and diagnostic medical uses. Peptides carrying radioactive agents are known to be therapeutically useful in the treatment of tumors.

An important diagnostic use of labelled peptides is as imaging agents. For example, U.S. Pat. No. 4,926,869 to Rubin et al. discloses detection of an inflammation site in an individual by administering to the individual a labelled immunoglobulin or fragment thereof. The labelled immunoglobulin accumulates at the site of inflammation, thereby permitting radiographic imaging of the site utilizing known imaging techniques.

Other publications which describe the imaging of sites of infection or inflammation, utilizing labelled peptides and peptides carrying radioactive agents, include International Patent Publication Nos. WO 90/10463 and WO 90/13317.

There remains a need in the art for labelled peptides and peptides carrying radioactive agents which can be utilized for medical purposes.

SUMMARY OF THE INVENTION

In accordance with the present invention, a labelled CXC chemokine is utilized to image a target site in an animal's body. The labelled CXC chemokine is introduced into the animal's body, and allowed to accumulate at a target site which has receptor molecules complementary to Interleukin-8. The accumulated, labelled CXC chemokine then is detected so as to image the target site.

DETAILED DESCRIPTION OF THE PREFERRED EMBODIMENTS

The present invention utilizes Interleukin-8 (IL-8) material, a member of the "CXC" family of chemotactic cytokines (or "chemokines"), an analog, homolog, derivative or fragment thereof, or a peptide having specificity for a receptor of Interleukin-8 (hereinafter sometimes referred to collectively as CXC chemokines, Interleukin-8 material or IL-8 material).

The CXC family of chemotactic cytokines includes, but is not limited to, Interleukin-8, Macrophage Inflammatory Protein-2 (MIP-2), Growth Regulated Gene Products (GRO) including $GRO_\alpha$, $GRO_\beta$ and $GRO_\gamma$, Melanoma Growth Simulating Activity (MGSA), Platelet Factor-4 (PF-4), Gamma-interferon Inducible Protein (gamma-IP), Platelet Basic Protein, Connective Tissue Activating Protein (CTAP-III), Beta-thromoboglobulin ($\beta$-TG), Neutrophil-activating Peptide-2 (NAP-2), Chicken v-src-inducible Protein (93), and Epithelial Cell-Derived Neutrophil-Activating Factor-78 (ENA-78).

In preferred embodiments, the CXC chemokine utilized is human Interleukin-8, or an analog, homolog, fragment or derivative thereof.

Human IL-8 is approximately 72 amino acid residues in length with a molecular weight of approximately 8 kD, although there are a 77 residue and a few other variant forms.

Members of the "CXC" family of cytokines (CXC chemokines) generally are basic heparin binding polypeptides having proinflammatory and reparative activities. Typical members of the group are 8–10 kD cytokines, and those members other than Interleukin-8 generally having at least about 20–45% homology with Interleukin-8.

Figure 1:
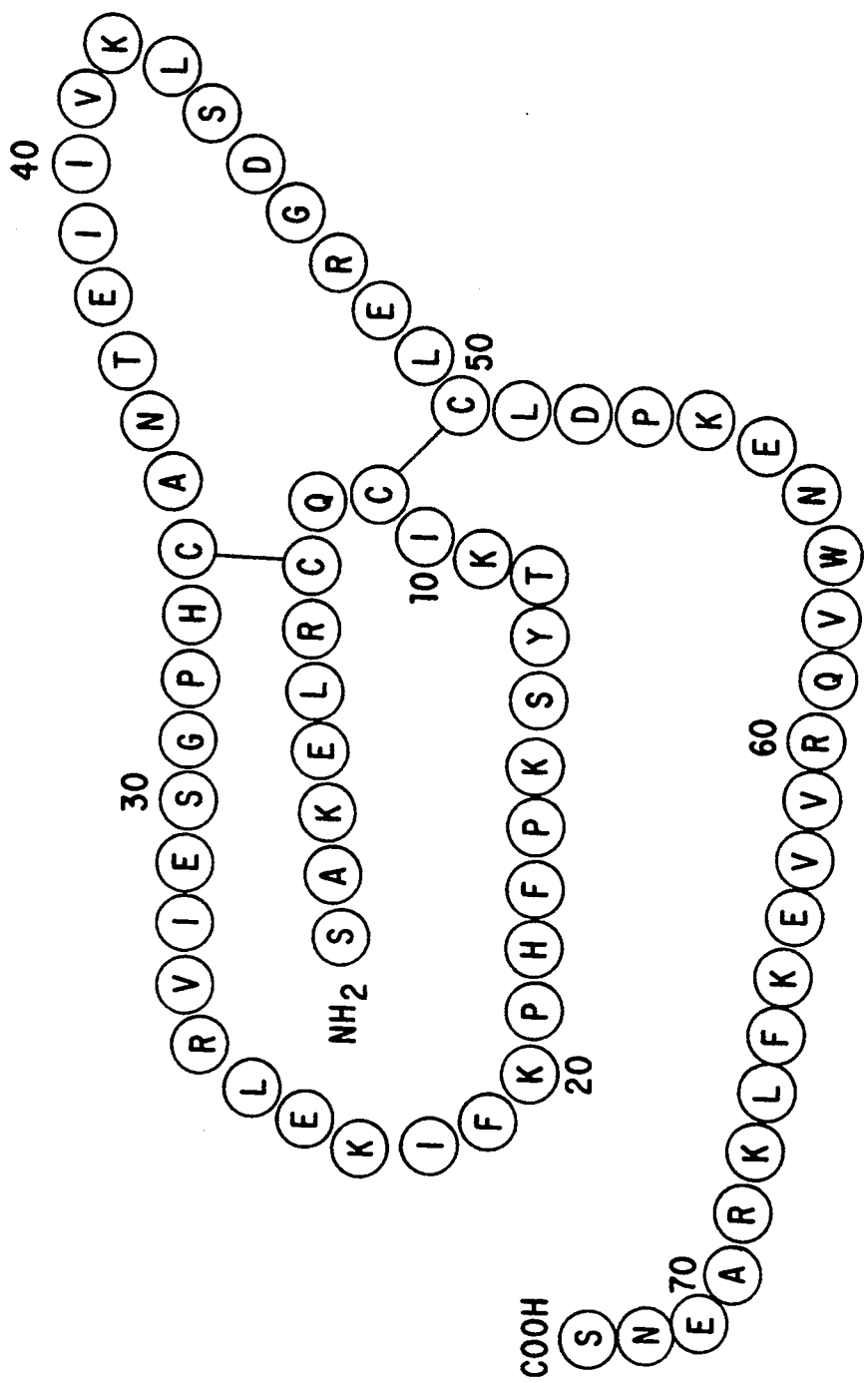
FIG. 1 is a schematic representation of an Interleukin-8 molecule capable of being utilized in accordance with the present invention.

The amino acid sequence of Interleukin-8 is shown in FIG. 1, wherein the circled letters represent amino acids as follows: A represents Alanine, R represents Arginine, N represents Asparagine, D represents Asparticacid, C represents Cysteine, Q represents Glutamine, E represents Glutamic acid, G represents Glycine, H represents Histidine, I represents Isoleucine, L represents Leucine, K represents Lysine, F represents Phenylalanine, P represents Proline, S represents Serine, T represents Threonine, W represents Tryptophan, Y represents Tyrosine and V represents Valine, or a suitable derivative thereof.

The members of the CXC chemokine family are generally characterized by having an ELR amino acid sequence immediately preceding a conserved C-X-C sequence with four cysteine residues, the first two being separated by a variable amino acid (X) therebetween.

The present invention is further applicable to derivatives of CXC chemokines in which retroinverse or other non-hydrolyzable linkages have been inserted, or D-amino acids substitutions have been made, in order to modify the native L-amino acid-containing sequence.

As noted above, the CXC chemokine carries a label or radioactive agent such as indium, iodine, technetium, rhenium, gallium, samarium, holmium, yttrium, copper, cobalt and the like. In particularly preferred embodiments, the CXC chemokine material carries a radioactive label selected from the group consisting of indium-111, iodine-123 and technetium-99m.

The CXC chemokine can employ any suitable means for carrying the label or radioactive agent. Known methods for labelling peptides include the conventional "post-formed chelate approach" and the more recent "pre-formed chelate approach" developed by Fritzburg et al., U.S. Pat. Nos. 4,965,392 and 5,037,630, incorporated herein by reference. In the "pre-formed approach," the chelating agent is complexed with a radionuclide and then conjugated to the peptide. In the "post-formed approach," the chelating agent is first conjugated to the peptide and the resulting conjugate is incubated with radionuclide along with a reducing agent.

Suitable chelating agents for use in the present invention include triamide thiolate (N₃S) chelating agents such as represented by formula (I) and (Ia) below, diamide dithiolate (N₂S₂) chelating agents such as represented by formula (II) below and diamide diphenolic chelating agents such as represented by formula (III) below:

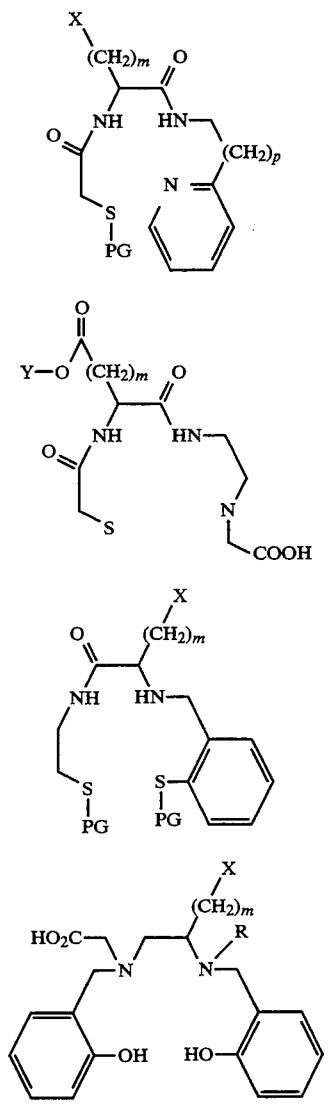

Wherein m in formulas (I), (Ia), (II) and (III) is a whole number of from 1 to about 10 (in formulas (I), (Ia) and (II), m preferably is about 3); P in formula (I) is either 0 or 1; Y of formula (Ia) is o- or p-nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, thiophenyl, tetrafluorothiophenyl, tetrafluorophenyl, thiophenyl, tetrafluorothiophenyl, o-nitro-p-sulfophenyl or N-hydroxyphthalimide, most preferrably tetrafluorophenyl; PG in formulas (I) and (II) is a suitable sulfur protecting group (each of which may be the same or different in formula II) selected from the group consisting of S-acyl groups of from 1 to about 20 carbon atoms such as alkanoyl, benzoyl and substituted benzoyl (wherein alkanoyl is preferred), S-alkyl groups of from 1 to about 20 carbon atoms such as benzyl, t-butyl, trityl, 4-methoxybenzyl and 2,4-dimethoxybenzyl (wherein 2,4-dimethoxybenzyl is preferred), alkoxyalkyl groups of from 1 to about 10 carbon atoms such as methoxymethyl, ethoxyethyl and tetrahydropyranyl (wherein tetrahydropyranyl is preferred), carbamoyl, and alkoxy carbonyl groups of from 1 to about 10 carbon atoms such as t-butoxycarbonyl, methoxycarbonyl and ethoxycarbonyl (wherein t-butoxycarbonyl is preferred); X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl, and N-alkoxycarbamoyl groups of from 1 to about 10 carbon atoms such as N-methyoxycarbamoyl and t-butoxycarbamoyl (wherein in formulas (I) and (II), N-methoxycarbamoyl is preferred); and R of formula (III) is selected from the group consisting of hydrogen and alkyl groups of from 1 to about 10 carbon atoms such as methyl and t-butyl (wherein t-butyl is preferred).

Suitable sulfur-protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are acyl groups of from 1 to about 20 carbon atoms, preferably alkanoyl or benzoyl. Other possible chelating compounds are described in the European Patent Application assigned publication number 0 284 071 incorporated herein by reference.

Synthesis of a radiolabelled chelating agent, such as a Tc-99m bifunctional chelate, and subsequent conjugation to the IL-8 material, can be performed as described in European Patent Application publication number 0 284 071 (supra), U.S. Pat. No. 4,965,392 (supra), and related technologies as covered by U.S. Pat. Nos. 4,837,003, 4,732,974 and 4,659,839, each incorporated herein by reference.

In accordance with one embodiment, the present invention comprises an IL-8 material conjugated with an unlabelled chelating agent, which later can be chelated with a suitable label or radioactive agent.

A lysine of the CXC chemokine can be utilized to carry indium-111. A tyrosine, iodophenyl derivative or lysine (using Bolton-Hunter reagent) of the CXC chemokine can be utilized to carry iodine-123. A lysine or added free cysteine of the CXC chemokine can be utilized to carry technetium-99m.

In another embodiment, the CXC chemokine is labelled with a radioactive agent such as iodine-123 utilizing chloramine-T hydrate.

In still another embodiment, the CXC chemokine is labelled with a radioactive agent such as indium-111 utilizing a chelating agent such as diethylenetriaminepentaacetic acid.

The CXC chemokine carries the label or radioactive agent to a target site of an animal, such as a human or other mammal.

In particularly preferred embodiments, radiolabelled CXC chemokine is injected into an animal's body and allowed to accumulate at a target site of inflammation and/or infection. Interleukin-8 has been found to be a very potent attractant for neutrophils produced by T-lymphocytes, monocytes, vascular endothelium and other tissues. Accordingly, radiolabelled Interleukin-8 is particularly suitable for imaging sites of inflammation and infectious disease in the body. Such sites include Interleukin-8 receptor molecules having areas which are complementary to corresponding Interleukin-8 material.

The radiolabelled CXC chemokine is injected into the subject in a pharmaceutically acceptable carrier, such as an aqueous medium. Generally, a diagnostically effective dosage of radiolabelled CXC chemokine will vary depending on considerations such as age, condition, sex, and extent of disease in the subject individual, counter indications, if any, and variables, to be adjusted by the individual physician. For example, dosage can vary from about 0.01 mg/kg to about 2000 mg/kg, and in more preferred embodiments from about 0.1 mg/kg to about 1000 mg/kg. Initial toxicologic experiments have demonstrated no significant pathology associated with the in vivo administration of IL-8.

The radiolabelled CXC chemokine begins to accumulate within approximately 15 minutes after injection into the subject, and in vivo imaging can be performed utilizing conventional imaging equipment up to 24 hours or more after injection. Known imaging methods include conventional gamma camera techniques, single photon emission computerized tomoprophy (SPECT), and other radionuclide scans.

After accumulating at the target site, the labelled CXC chemokine is gradually cleared from the target site and the animal's system by normal bodily function.

The invention is further illustrated by the following examples, which are not intended to be limiting.

EXAMPLE 1

Radiolabeling of Interleukin-8 with Technetium-99m

A solution of CXC chemokine such as IL-8 (0.01 mmol), in 2 mL of carbonate/bicarbonate buffer at pH 8.5±0.5 is treated with a solution of 0.1 mmol of the ligand of formula I above (wherein m=2, p=1, PG is benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired IL-8 conjugate.

EXAMPLE 2

A solution of CXC chemokine such as IL-8 (0.01 mmol), in 2 mL of carbonate/bicarbonate buffer at pH 8.5±0.5 is treated with a solution of 0.1 mmol of the ligand of formula (II) above (wherein m=2, both PG are benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired IL-8 conjugate.

EXAMPLE 3

A solution of CXC chemokine such as IL-8 (0.01 mmol) in 2 mL of carbonate/bicarbonate buffer at pH 8.5±0.5 is treated with a solution of 0.1 mmol of the ligand of formula (III) above (wherein m=4, X is succinimidyloxycarbonyl and R is hydrogen) in dimethylformamide (0.5 mL) and the entire mixture is kept at room temperature for 2 hours. The mixture is then diluted with water (2.5 mL) and dialyzed extensively against water or 0.1M ammonium bicarbonate, pH 7.5. After dialysis, the solution is lyophilized to give the desired IL-8 conjugate.

EXAMPLE 4

To 100 uL of a solution containing 5 mg of sodium gluconate and 0.1 mg of stannous chloride in water, 500 ul of 99m-TcO4 (pertechnetate) is added. After incubation for about 10 minutes at room temperature, a solution of 500 uL of the IL-8 conjugate (1 mg/mL in 0.1M carbonate/bicarbonate buffer, pH 9.5) of Example 1 or 2 is then added and the entire mixture is incubated at 37° C. for about 1 hour. The desired labelled peptide is separated from unreacted 99mTc-gluconate and other small molecular weight impurities by gel filtration chromatography (Sephadex G-50) using phosphate buffered physiological saline, (hereinafter PBS), 0.15M NaCl, pH 7.4 as eluent.

EXAMPLE 5

A mixture of gentisic acid (25 mg), inositol (10 mg), and the IL-8 conjugate of Example 3 (500 uL, 1 mg/mL in water) is treated with In-111 indium chloride in 0.05M HCl. The solution is allowed to incubate at room temperature for about 30 minutes. The desired labelled peptide is separated from unreacted In-111 indium salts and other small molecular weight impurities by gel filtration chromatography (Sephadex G-50) using phosphine buffered physiological saline, (PBS), 0.15M NaCl as eluent.

EXAMPLE 6

Radioiodination of Interleukin-8, chloramine-T hydrate method

The following reagents and materials are prepared for radioiodination of Interleukin-8:

A) Chloramine-T Hydrate (freshly prepared) (FW=227.7) (Store stock desiccated, in vacuo, in dark, ambient temperature)
  1. Weigh out 10.0 mg and dilute with 5.0 ml of 0.05M Phosphate Buffer, pH 6.8.
  2. Take 1.0 ml of dilution and add 9.0 ml 0.05M Phosphate Buffer, pH 6.8 in volumetric flask.
  3. Concentration=0.2 mg/ml; use 45 $\mu$/exp.=39.5 nmoles.

B) 0.05M Sodium Phosphate Buffer, Dibasic, pH 6.8. (FW=268.07) (For Chloramine-T, Metabisulfite, dilution and Reaction).
  1. Weigh out 1.3404 gm and dilute to 80 ml (H$_2$O).
  2. Adjust pH to 6.8, bring to total volume of 100 ml in volumetric flask.

C) 0.25M Sodium Phosphate Buffer, Dibasic, pH 6.8. (FW=268.07) (Reagent for buffering NaI-123 during reaction).
  1. Weigh out 6.7018 gm and dilute to 80 ml (H$_2$O).
  2. Adjust pH to 6.8, bring to total volume of 100 ml in rolmeric flask.

D) Sodium Metabisulfite (Freshly Prepared) (FW=190.1).
1. Weigh out 20.0 mg and dilute with 5.0 m of 0.05M Sodium Phosphate Buffer.
2. Take 1.0 ml of this solution and add 9.0 ml 0.05M Sodium Phosphate Buffer.
3. Concentration=0.4 mg/ml; use 45 µl=18.0 µg/exp.=94.5 nmoles.

E) Phosphate Buffered Saline
1. Dissolve Sigma (PBS) prepared powder in 1.0 liter of millipore $H_2O$. Sigma cat. # 1000-3.
2. Check pH, should be 7.4.

F) BioRad AG1-X8 Artion Resin 100–200 mesh, Acetate form.
1. Prepare slurry by suspending 6.4 gms of resin in 10 ml PBS.

G) Potassium Iodide Solution
(For testing Chloramine-T solution before use in reaction)
1. Weight out 0.25 gm KI and dilute with 5.0 ml ($H_2O$).
2. Add several drops of the Chloramine-T solution to the KI solution.
3. A color change from a clear to light yellow solution should be observed, if the Chloramine-T solution is reactive.

H) Microfuge Tubes
1. Sigma siliconized, 1.7 ml, polyproylene, Cat. # T-3406.

I) Sodium Iodine-123
1. Mallinckrodt Medical, Inc.

J) Interleukin-8 (assuming FW=8,000)
1. Use 10 µg per radioiodination=1.25 nmoles. Pepro Tech Inc.

The following preparations are undertaken prior to running the reaction:

A slurry is prepared of 90% v/v BioRad AG1-X8, 100–200 mesh, acetate form, 24 hours prior to use, with Phosphate Buffered Saline. 2.0 ml of the slurry is poured into a small AG1-X8 column, which then is washed with 10.0 ml Phosphate Buffered Saline. 45.0 µl Chloramine-T (freshly prepared), is pre-drawn into a Hamilton syringe after testing it with 5.0% KI. 45.0 µl Metabisulfite (freshly prepared) is pre-drawn into a Hamilton syringe. 50.0 µl Phosphate Buffered Saline is pre-drawn into a tuberculin syringe, and the syringe is labelled "R". 10.0 ml of Phosphate Buffered Saline is poured into a beaker, and set beside the column, for elution of the column.

Interleukin-8 is labelled with iodine-123 as follows:
To a siliconized microfuge tube reaction vial (1.7 ml), add (12.5 µg) IL-8 in 0.125 ml 0.05M Phosphate Buffer, pH 6.8. Add (50.0 µl) 0.25M Phosphate Buffer, pH 6.8 to the reaction vial and gently swirl. Add (20 µl) 20 nanograms "cold" iodide and gently swirl. Add (10–20 µl), 2.0 mCi, NaI-123 to the reaction vial and gently swirl. Add (45.0 µl) of Chloramine-T to the reaction vial, with a pre-drawn Hamilton syringe, and gently swirl. Incubate for 1.5 minutes at room temperature.

Add (45.0 µl) of Metabisulfite to the reaction vial, with a pre-drawn Hamilton syringe, and gently swirl. Assay reaction vial on a Capintec dose calibrator.

After reaction mixture has been assayed, place entire volume on prepared AG1-X8 column. Add (50 µl) PBS to reaction vial and swirl, then add to reaction mixture on column. Unplug column and collect 8 drops in the first tube. Then collect 2 drops in the next 24 tubes. The Vo will be in approximately tube # 6. Use 1.7 ml siliconized microfuge tubes. Assay collected fractions on the Capintec dose calibrator. Combine the major fractions starting at the void volume. (NOTE: An aliquot should be taken for a dose assay for accurate results, if tissue distribution studies are being done.) Run TLC of sample in order to observe any free I-123. Spot a very small aliquot on a Gelman ITLC-SG strip, and develop with N-saline for 8 to 10 minutes. Cut into 1.0 cm sections and count on auto-gamma counter. Unreacted 1-123 migrates at or near solvent front, protein remains at origin, small peptides have varying Rf values, at or near the origin.

EXAMPLE 7

Indium-111 Radiolabelling of Interleukin-8

The following reagents and materials are prepared prior to running the reaction:

A) Cyclic-Diethylenetriaminepentaacetic acid dianhydride (C-DTPA), FW—357.22 is synthesized and kept in a desiccator, in vacuo, at room temperature.

B) Commercially available Dimethylsulfoxide anhydrous (DMSO) is further purified by fractional freezing at or below 18.4° C. 20 to 25 ml of DMSO is placed in an oven dried 100 ml bottle and tightly capped. The bottle is placed in a slurry ice water bath and swirled until liquid solidifies on the walls of the bottle. An oven dried Pasteur pipet is used to remove remaining liquid. The bottle is capped and stored at room temperature under nitrogen, in a desiccator. Aldrich, 27, 685-5.

C) Nitrogen Gass is grade # 5. Airco

D) Phosphate Buffered Saline (PBS)
1. Dissolve Sigma (PBS) prepared powder in 1.0 liter of millipore water.
2. Check pH, should be 7.4 Sigma, 1000-3

Phosphate Buffered Saline+5.0% BSA (For equilibration of G-25 column)
1. To 10.0 ml PBS dissolve 0.5 g BSA.
2. Final concentration 50.0 mg/ml BSA.

F) Phosphate Buffered Saline+0.5% BSA (For elution of G-25 column)
1. To 50.0 ml PBS dissolve 0125 g BSA.
2. Final concentration 5.0 mg/ml BSA.

G) G-25, medium grade
1. Weigh out desired amount and swell in PBS for 24 hours.
2. Before use degas for 24 or more hours.
3. 24 hours prior to radiolabelling pour columns and equilibrate and wash with BSA/PBS solutions.
4. Size of columns to be determined experimentally.

H) 0.10M diethylentriaminepentaccetic acid (DTPA), FW=393.20
1. Weigh out 0.393 gm DTPA and place in 8.0 ml PBS.
2. Adjust pH to 5.4, bring to total volume of 10.0 ml in a volumetric flask. (Needs to become acidic for solubility) Sigma, D-6518

I) Millipore water

J) 111-Indium chloride (111-InCl3) in 0.05N HCl Nordion International, Kanata, Canada, T209A (NOTE: In order to avoid hydrolysis and trace metal contamination, all reagents should be of the highest purity, DMSO should be purified by fractional freezing, all glassware and instruments should be thoroughly cleaned and rinsed approximately three times with millipore filtered water, and glassware and instruments to be used in the chelation reaction should be oven dried for approximately 24 hours at about 140° C. and cooled in a desiccator.)

The reaction is run as follows:

In step 1, C-DTPA (11,075 mg) is dissolved in 5.0 ml anhydrous DMSO. The tube is covered with parafilm, and gently inverted until the solution becomes clear. To 10 µg lyophilized IL-8 is added 0.5 ml PBS, pH 7.4. Add 0.01 ml (22.32 µg) C-DTPA/DMSO from step # 1. Incubate solution, at room temperature, for 50 minutes. Gently swirl solution every 15 minutes. After incubation, place entire volume on the prepared G-25 column. Collect 0.20 ml fractions. Combine fractions at Vo and several fractions after the void volume. For Vo determination, use blue dextran. 111-InC13 is assayed on a Capintec dose calibrator and 1.0 to 2.0 mCi of 111-In is pipetted into the IL-8 tube. The tube is gently swirled and assayed for the amount of radioactivity. The 111-In/IL-8 solution is incubated for 30 minutes, at room temperature. Excess 111-In is chelated to prevent the formation of indium hydroxide, an insoluble precipitate. The reaction mixture on a G-25 column and eluted with either PBS or 0.50% BSA, PBS. 0.20 ml fractions are collected. Fractions are assayed either on the dose calibrator or dilute aliquots of the fractions for counting on the gamma counter. Combine the fractions at the Vo (protein peak) and fractions after the void volume until the radioactivity levels decline. The excess chelated 111-In is eluted at or near the Vt. The combined Vo fractions are assayed on the dose calibrator and the radiolabelling efficiency are calculated. The empty reaction tube is also assayed to assure transfer of the majority of radioactivity.

EXAMPLE 8

Imaging with radiolabelled Interleukin-8

White, male, Sprague-Dawley rats, weighing between 250 and 350 gm were used for imaging of inflammatory lesion. The lesion was induced by injecting 300 µl of 2.0% carrageenan (iota form), suspended in n-saline, into the hind limb. The other hind limb was used as a control and was injected with 300 µl saline. The hind limbs were selected, instead of IP or Sub-Q injections of carrageenan on the body of the rats, because less background activity is present for these studies.

The lesion was induced at various times prior to the injection of the radiolabelled IL-8. A difference in uptake of radioactivity was observed in the carrageenan limb, as compared to the control limb, when the radiolabelled IL-8 was injected 3 hours to 24 hours post lesion induction.

Routinely, images were acquired serially every 15 minutes for 3.0 hours post radiolabel injection. 15 minute images were also acquired every 24 hours post injection, until the labelled was cleared from the animal.

Figure 2A:
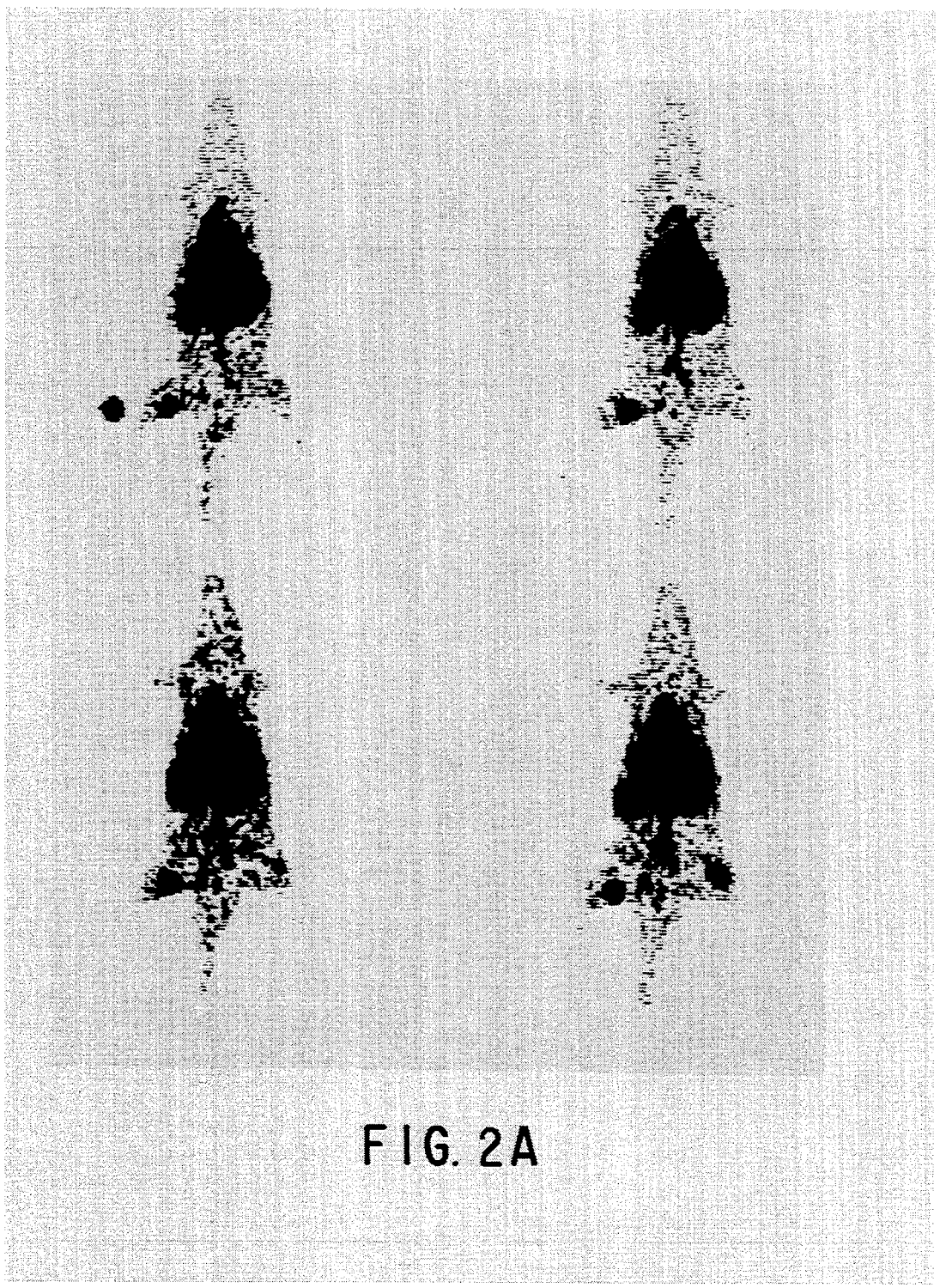
FIG. 2A shows images of accumulation of indium-111 radiolabelled Interleukin-8 in an inflammatory lesion induced in a thigh of a rat at 15 minutes, 30 minutes, 45 minutes and 1 hour post-injection.
Figure 2B:
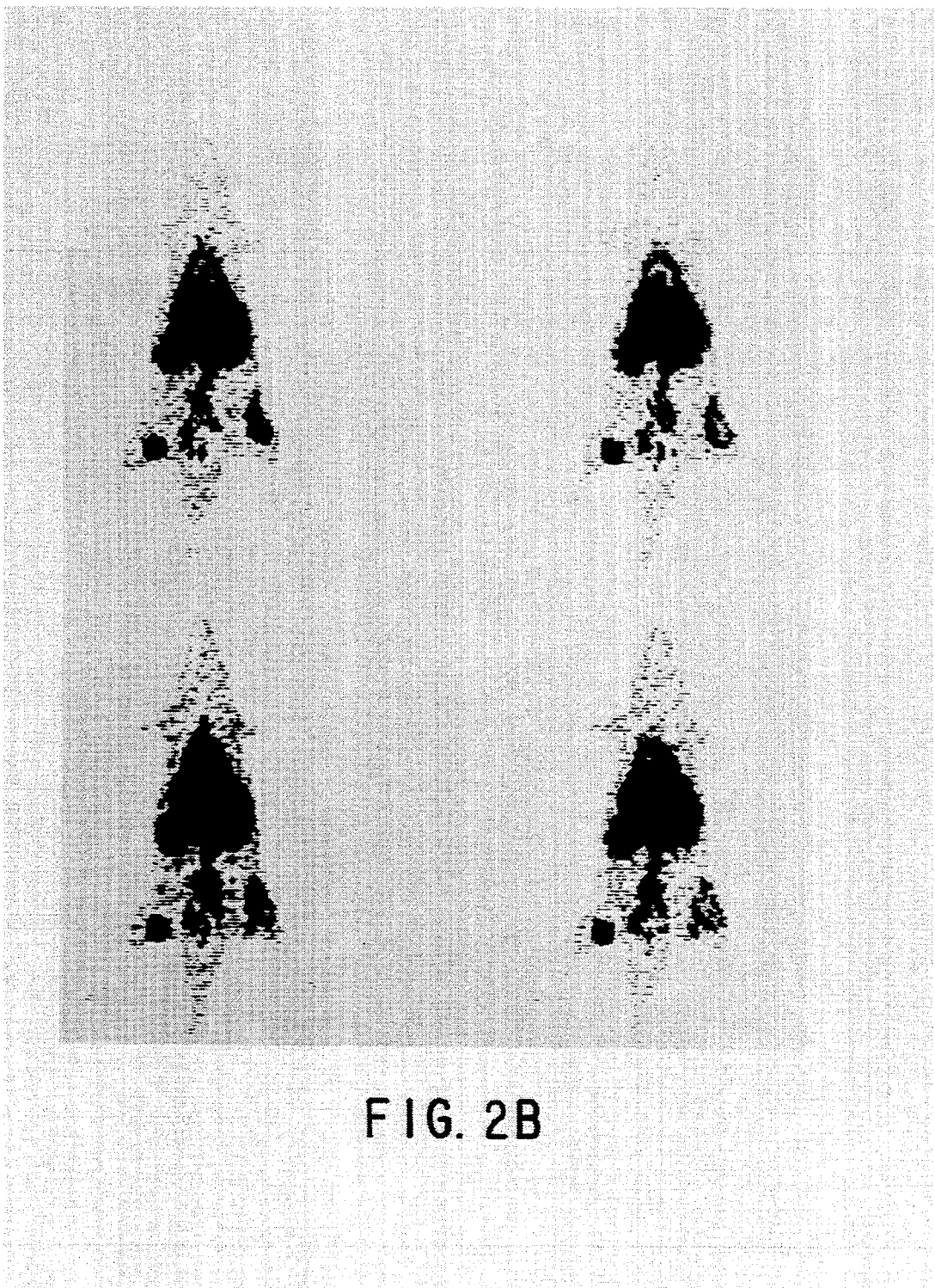
FIG. 2B shows images as in FIG. 2A at 1 hour 15 minutes, 1 hour 30 minutes, 1 hour 45 minutes and 2 hours post-injection.
Figure 2C:
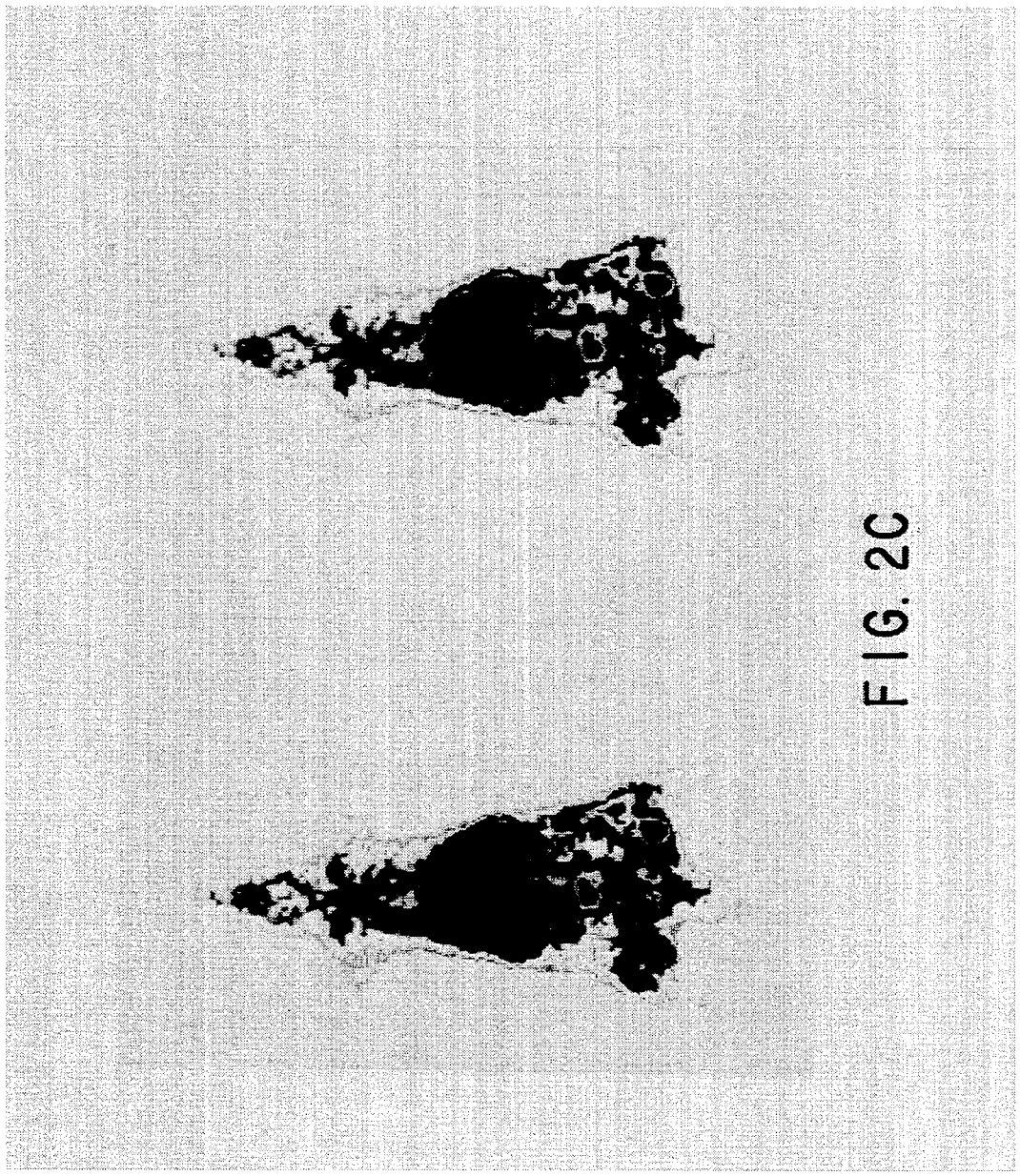
FIG. 2C shows images as in FIG. 2B at 24 hours post-injection.
Figure 3A:
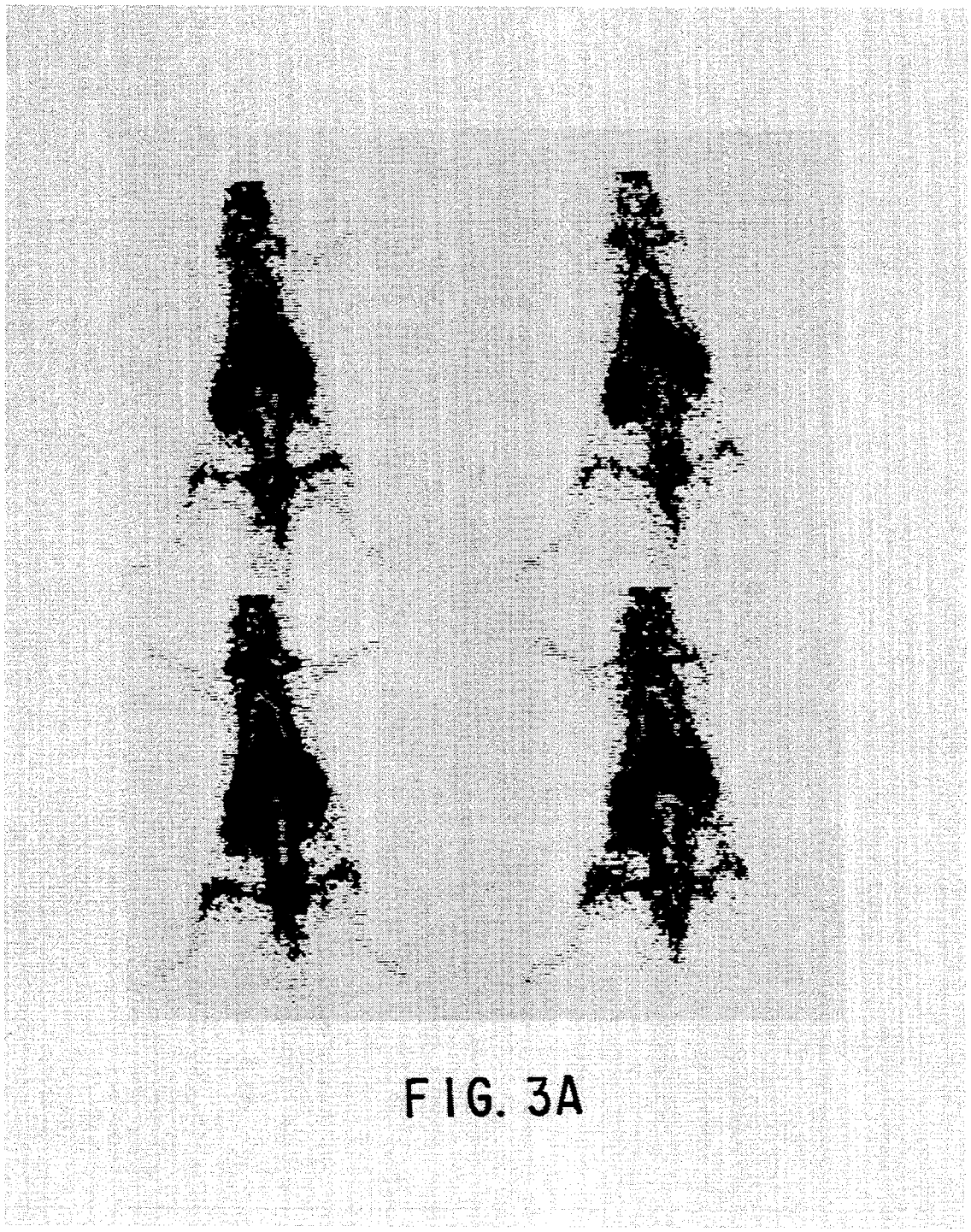
FIG. 3A shows images of accumulation of iodine-123 radiolabelled Interleukin-8 in an inflammatory lesion induced in a thigh of a rat at 15 minutes, 30 minutes, 45 minutes and 1 hour post-injection.
Figure 3B:
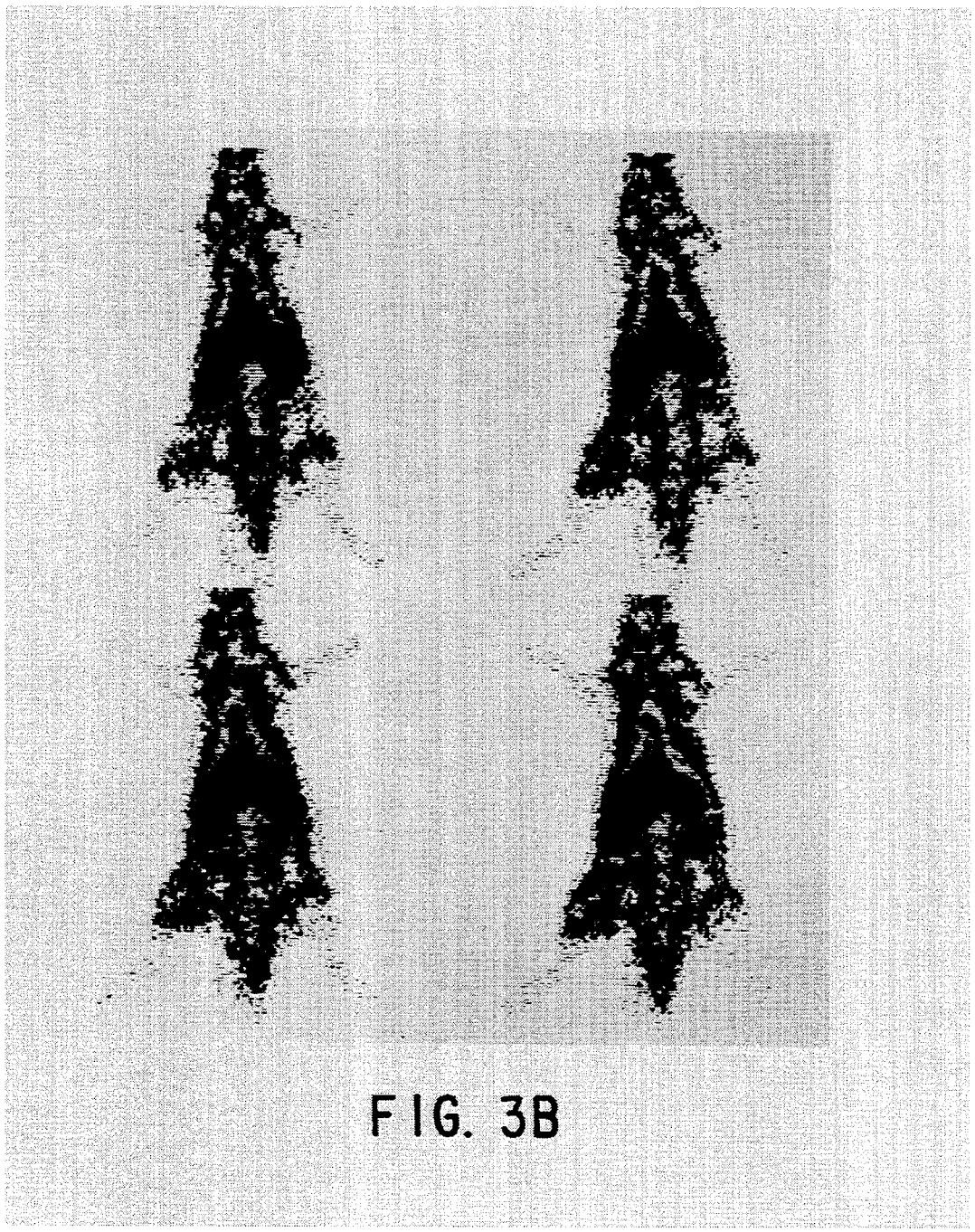
FIG. 3B shows images as in FIG. 3A at 1 hour 15 minutes, 1 hour 30 minutes, 1 hour 45 minutes and 2 hours post-injection.
Figure 3C:
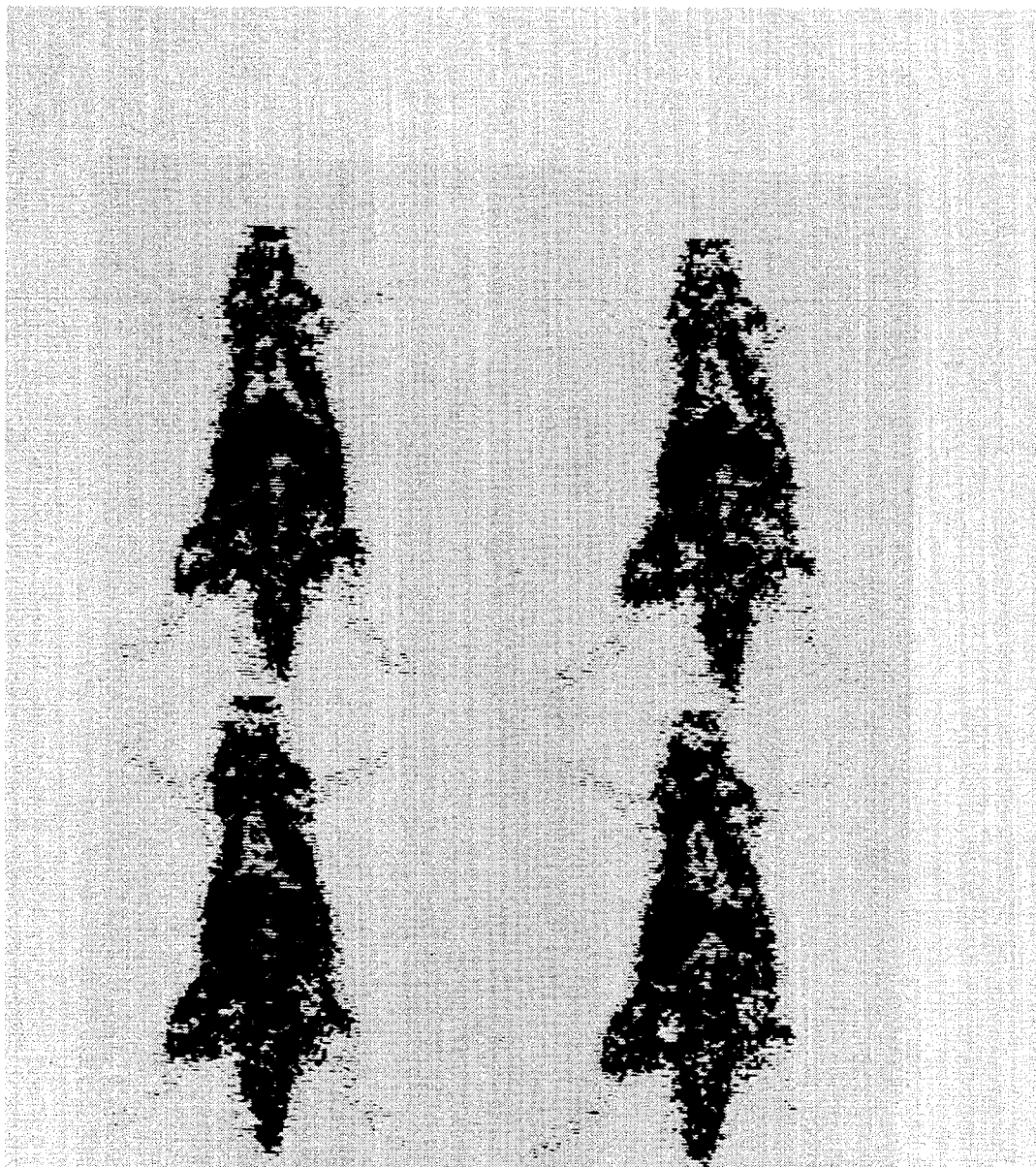
FIG. 3C shows images as in FIG. 3B at 2 hours 15 minutes, 2 hours 30 minutes, 2 hours 45 minutes and 3 hours post-injection.
Figure 3D:
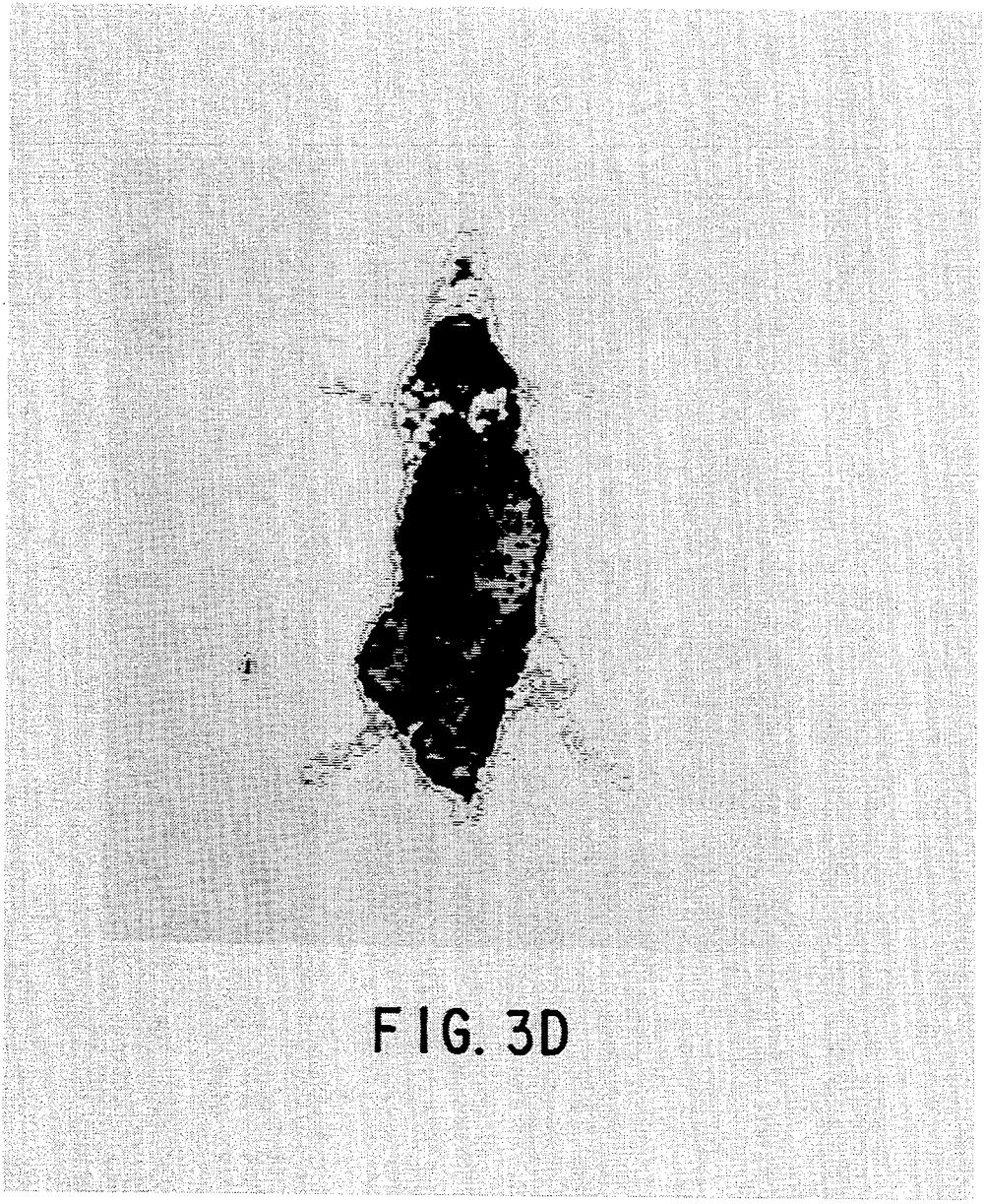
FIG. 3D is an image corresponding to those shown in FIG. 3C at 24 hours post-injection.

Different cameras and collimators were used, depending on the radionuclide. With 123-I and 111-In, a Siemens, ZLC Orbiter camera and a 140 Key, high resolution or medium energy collimators were respectively used. Image acquisition and storage, on all cameras, was accomplished by a Siemens MicroDelta computer, connected to a larger MicroVAX unit. FIGS. 2 and 3 show accumulation of radiolabelled IL-8 when labeled with In-111 and I-123 respectively.

Interleukin-8 material, when carrying a label or radioactive agent in accordance with the present invention, is particularly suitable for imaging sites of inflammation and infectious disease. Since many modifications, variations and changes in detail may be made to the described embodiments, it is intended that all matter in the foregoing description and shown in the accompanying drawings be interpreted as illustrative and not in a limiting sense.

---

We claim:

1. A method of imaging a target site in an animal body, comprising providing a radionuclide-labelled CXC chemokine, wherein C stands for cysteine and X stands for an amino acid, introducing a detectable amount of said labelled CXC chemokine into an animal's body, allowing the labelled CXC chemokine to accumlate at a target site of the animal's body, wherein neutrophils having Interleukin-8 receptor molecules are located at said target site, and detecting the accumulated, labelled CXC chemokine so as to image said target site.

2. The method of claim 1 wherein said target site is an inflamed or diseased portion of said animal's body.

3. The method of claim 1 wherein said labelled CXC chemokine is radiolabelled CXC chemokine.

4. The method of claim 3 wherein said CXC chemokine is labelled with indium-111, iodine-123, technetium-99m or copper-62.

5. The method of claim 4 wherein said indium-111 is carried by a lysine of said CXC chemokine.

6. The method of claim 4 wherein said CXC chemokine is labelled with indium-111 utilizing a chelating agent.

7. The method of claim 6 wherein said chelating agent is C-DTPA.

8. The method of claim 6 wherein said CXC chemokine is human Interleukin-8.

9. The method of claim 4 wherein said iodine-123 is carried by a tyrosine, iodophenyl derivative or lysine of said CXC chemokine.

10. The method of claim 4 wherein said CXC chemokine is labelled with iodine-123 utilizing chloramine-T hydrate.

11. The method of claim 10 wherein said CXC chemokine is human Interleukin-8.

12. The method of claim 4 wherein said CXC chemokine is labelled with technetium-99m.

13. The method of claim 12 wherein said technetium-99m is carried by a lysine or an added free cysteine of said CXC chemokine.

14. The method of claim 1 wherein said CXC chemokine is labelled utilizing a chelating agent.

15. The method of claim 14 wherein said chelating agent is a triamide thiolate ligand, a diamide dithiolate ligand or a diamide diphenolic ligand.

16. The method of claim 15 wherein said CXC chemokine is labelled with technetium-99m or copper-62 and said chelating agent is a triamide thiolate ligand.

17. The method of claim 12 wherein said CXC chemokine is human Interleukin-8.

18. The method of claim 1 wherein said CXC chemokine is human Interleukin-8.

19. A method of delivering a labeling agent to a target site of an animal's body, comprising introducing into an animal's body a CXC chemokine carrying a radionuclide labeling agent, wherein C stands for cysteine and X stands for an amino acid, and allowing the labeling agent-carrying CXC chemokine to accumulate at a target site, wherein neutrophils having Interleukin-8 receptor molecules are located at said target site, so as to deliver said labeling agent to said target site.

20. A method of delivering a radioactive agent to a target site of an animal's body comprising introducing into an animal's body a CXC chemokine carrying a radioactive agent, wherein C stands for cysteine and X stands for an amino acid, and allowing the radioactive agent-carrying CXC chemokine to accumulate at a target site, wherein neutrophils having Interleukin-8 receptor molecules are located at said target site, so as to deliver said radioactive agent to said target site.

21. A composition comprising a CXC chemokine carrying a radioactive labeling agent, wherein said radioactive labeling agent is selected from the group consisting of indium-111, and technetium-99m.

22. The composition of claim 21 wherein said CXC chemokine is labelled with said radioactive labeling agent by utilizing a chelating agent which is conjugated to said CXC chemokine.

23. The composition of claim 22 wherein said chelating agent is a triamide thiolate ligand, diamide dithiolate ligand or diamide diphenolic ligand.

* * * * *

UNITED STATES PATENT AND TRADEMARK OFFICE
CERTIFICATE OF CORRECTION

PATENT NO. : 5,346,686
DATED     : September 13, 1994
INVENTOR(S) : Leon R. LYLE et al.

It is certified that error appears in the above-indentified patent and that said Letters Patent is hereby corrected as shown below:

On the title page item [73], change "Curators of the University of Michigan" to --Regents of the University of Michigan--.

Signed and Sealed this

Nineteenth Day of September, 1995

Attest:

BRUCE LEHMAN

*Attesting Officer*        *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser  Ala  Lys  Glu  Leu  Arg  Cys  Gln  Cys  Ile  Lys  Thr  Tyr  Ser  Lys  Pro
 1                    5                        10                       15

Phe  His  Pro  Lys  Phe  Ile  Lys  Glu  Leu  Arg  Val  Ile  Glu  Ser  Gly  Pro
                20                        25                       30

His  Cys  Ala  Asn  Thr  Glu  Ile  Ile  Val  Lys  Leu  Ser  Asp  Gly  Arg  Glu
           35                        40                       45

Leu  Cys  Leu  Asp  Pro  Lys  Glu  Asn  Trp  Val  Gln  Arg  Val  Val  Glu  Lys
      50                        55                       60

Phe  Leu  Lys  Arg  Ala  Glu  Asn  Ser
 65                        70
```